US008682115B2

(12) United States Patent
Heidrich et al.

(10) Patent No.: US 8,682,115 B2
(45) Date of Patent: Mar. 25, 2014

(54) OPTICAL SENSOR

(75) Inventors: Helmut Heidrich, Berlin (DE); Peter Lutzow, Berlin (DE); Herbert Venghaus, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 468 days.

(21) Appl. No.: 13/123,452

(22) PCT Filed: Oct. 7, 2009

(86) PCT No.: PCT/EP2009/007302
§ 371 (c)(1),
(2), (4) Date: Apr. 8, 2011

(87) PCT Pub. No.: WO2010/040565
PCT Pub. Date: Apr. 15, 2010

(65) Prior Publication Data
US 2011/0194807 A1    Aug. 11, 2011

(30) Foreign Application Priority Data
Oct. 9, 2008   (DE) .......................... 10 2008 050 767

(51) Int. Cl.
*G02B 6/00*    (2006.01)
(52) U.S. Cl.
USPC .................................. 385/12; 385/13; 385/42
(58) Field of Classification Search
USPC ..................................................... 385/12, 13
See application file for complete search history.

(56) References Cited

U.S. PATENT DOCUMENTS

| 5,324,933 | A | 6/1994 | Berkcan |
| 5,787,212 | A | 7/1998 | Hong et al. |
| 6,507,684 | B2 | 1/2003 | Tapalian et al. |
| 6,625,356 | B2 * | 9/2003 | Ticknor et al. .................. 385/39 |
| 6,657,731 | B2 | 12/2003 | Tapalian et al. |
| 6,721,053 | B1 | 4/2004 | Maseeh |

(Continued)

FOREIGN PATENT DOCUMENTS

| WO | WO0201146 A1 | 1/2002 |
| WO | WO2007084600 A1 | 7/2007 |

(Continued)

OTHER PUBLICATIONS

International Search Report and Written Opinion issued in PCT/EP2009/007302, mailed Jan. 29, 2010, 21 pages, with English translation.

*Primary Examiner* — Hemang Sanghavi
(74) *Attorney, Agent, or Firm* — Faegre Baker Daniels LLP

(57) ABSTRACT

An optical sensor for detecting a substance includes a first waveguide and a second waveguide optically coupled via a directional coupler to the first waveguide. The sensor has a functional surface in a region of the directional coupler for accumulating or storing the substance to be detected so that an intensity of a coupling arranged by the directional coupler between the first waveguide and the second waveguide can be changed by the accumulating or storing of this substance. The first waveguide extends in a freely floating manner over a coupling path covered by the directional coupler or rests on a swellable material. The first waveguide is guided in a vicinity of the coupling path so that a spacing between the first waveguide and the second waveguide can be changed there by a deformation or movement of the first waveguide or of a carrier of the first waveguide.

16 Claims, 14 Drawing Sheets

(56) References Cited

U.S. PATENT DOCUMENTS

| | | |
|---|---|---|
| 7,095,010 B2 | 8/2006 | Scherer et al. |
| 7,446,880 B2 | 11/2008 | Vollmer et al. |
| 2002/0172457 A1 | 11/2002 | Tapalian et al. |
| 2004/0023396 A1 | 2/2004 | Boyd et al. |
| 2005/0035278 A1 | 2/2005 | Margalit et al. |
| 2007/0242916 A1* | 10/2007 | Said et al. ............... 385/12 |
| 2008/0012997 A1 | 1/2008 | Reuter |
| 2013/0142477 A1* | 6/2013 | Diemeer ............... 385/12 |

FOREIGN PATENT DOCUMENTS

| | | |
|---|---|---|
| WO | WO2008054170 A1 | 5/2008 |
| WO | WO2008070399 A2 | 6/2008 |
| WO | WO2008070438 A1 | 6/2008 |

* cited by examiner

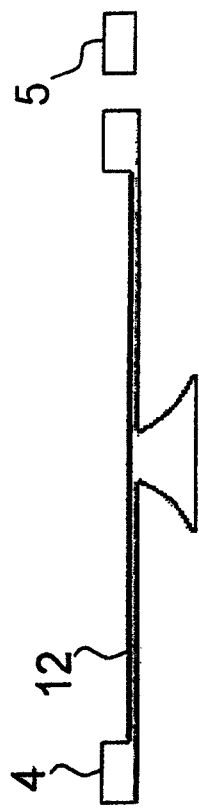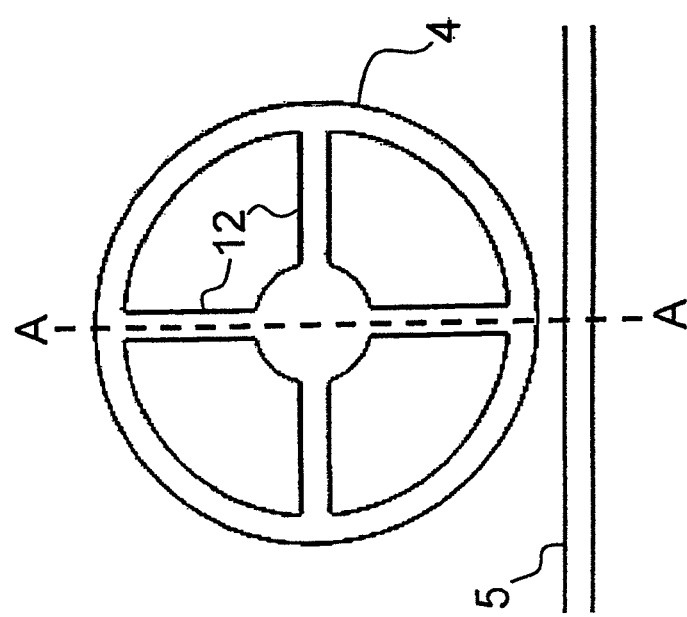
Fig. 12B
Fig. 12A

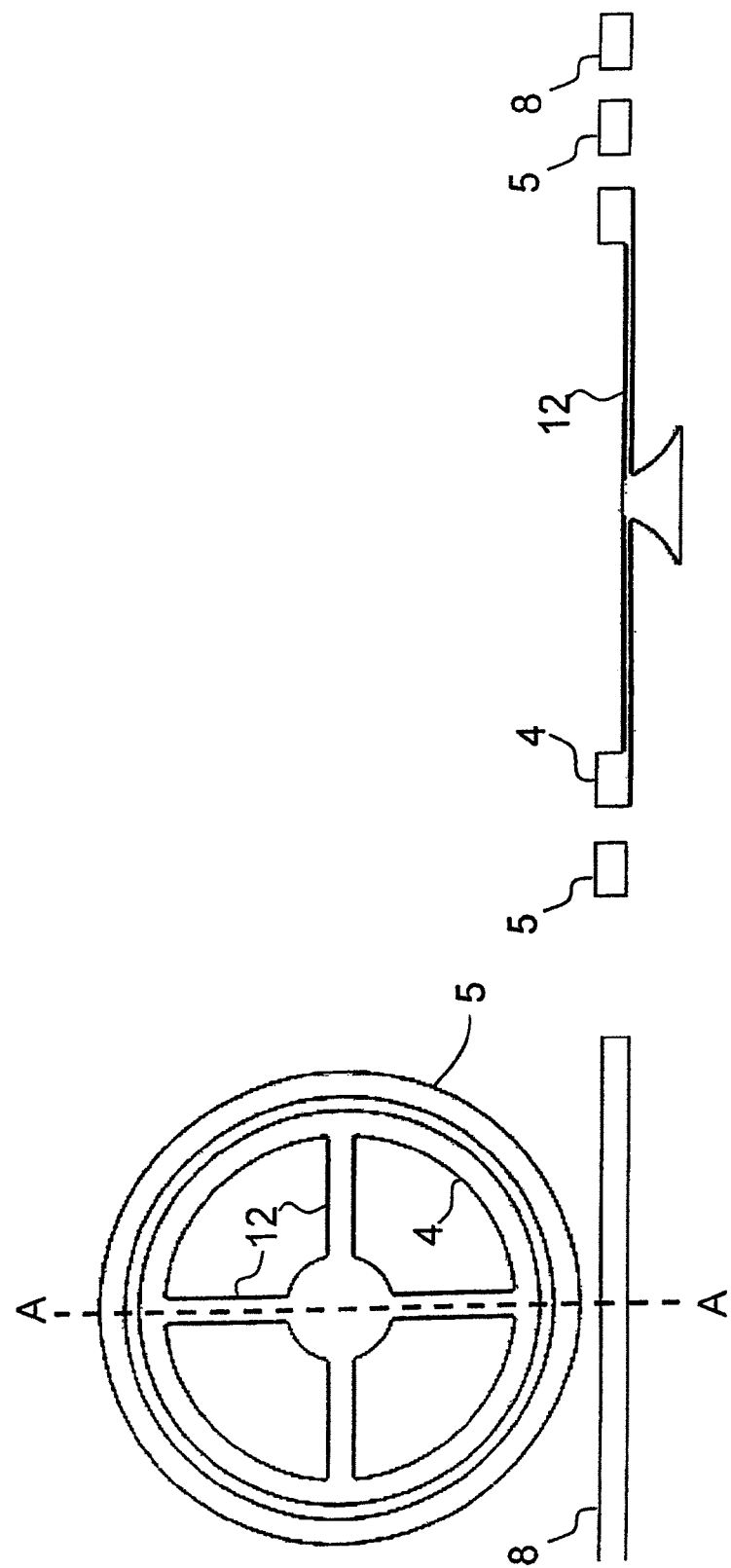

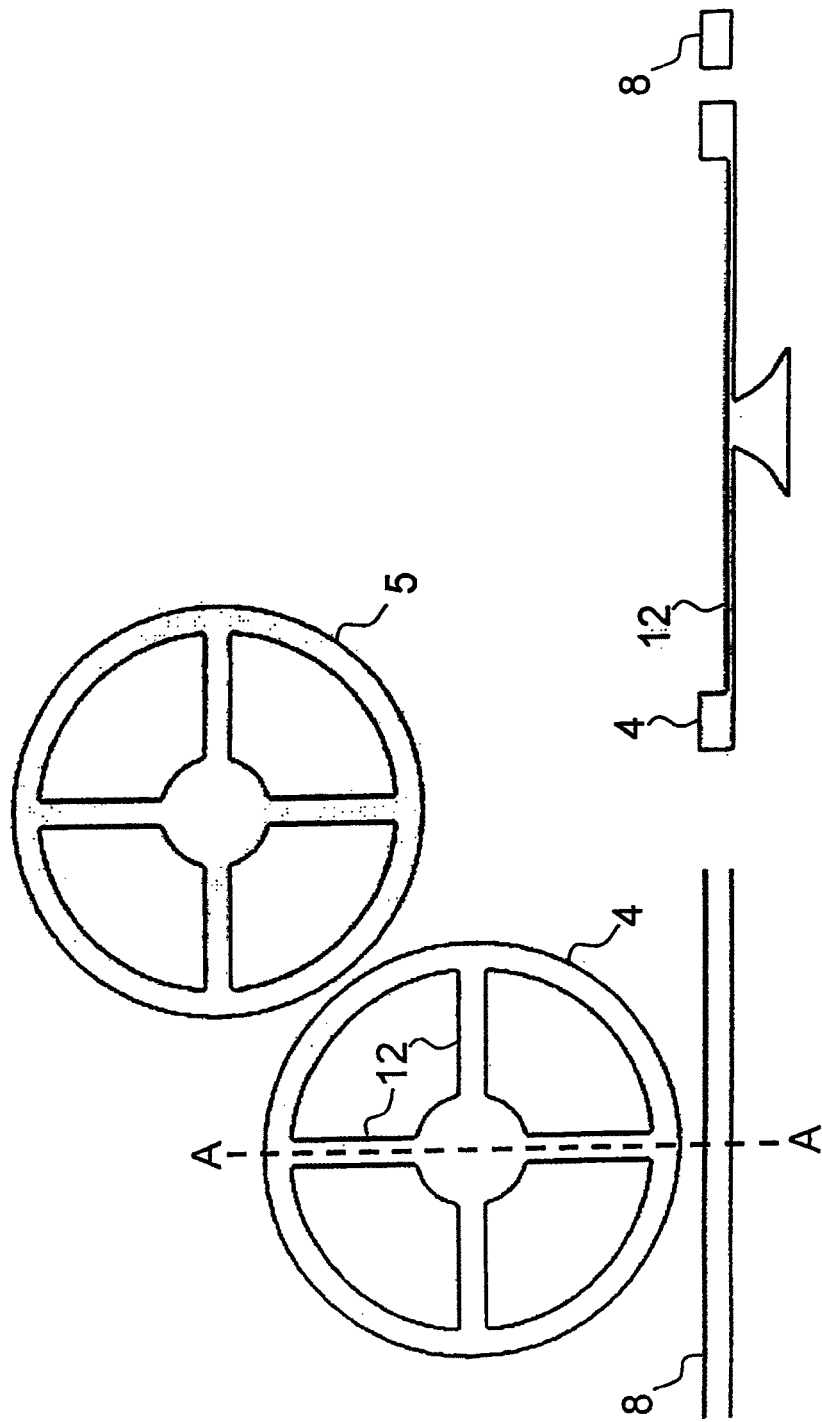

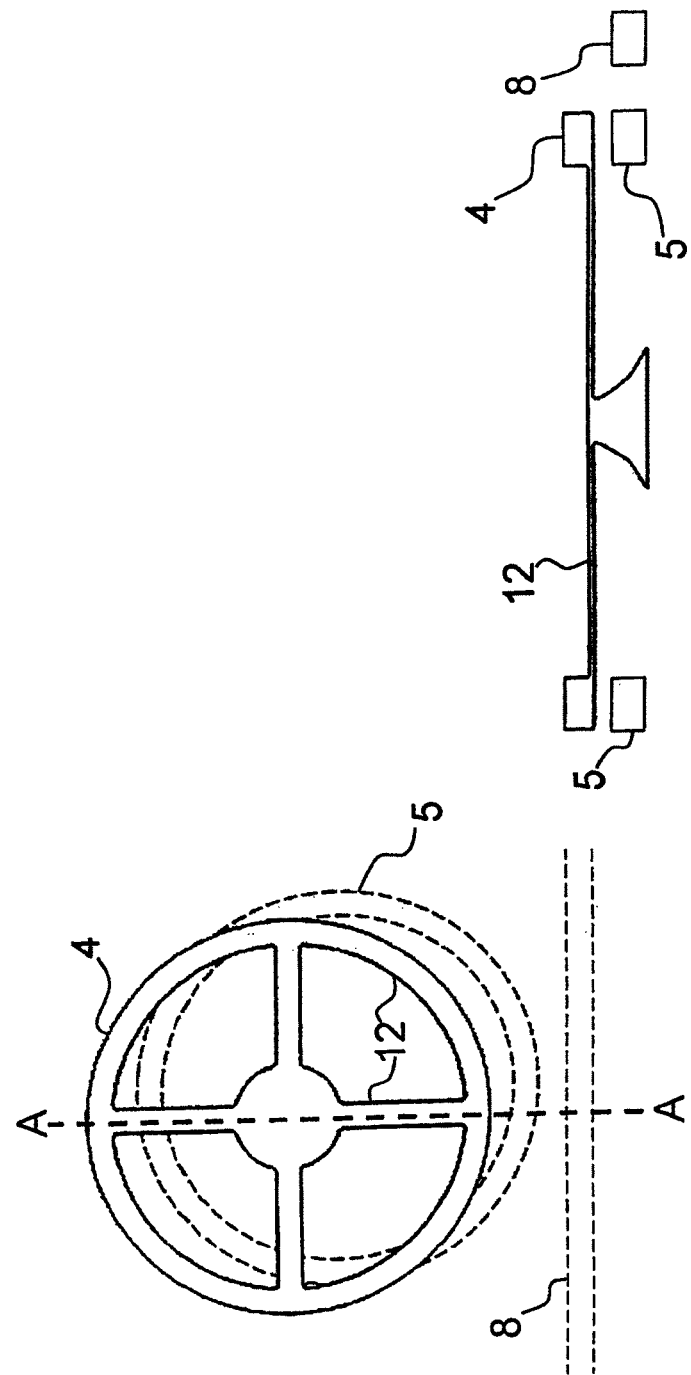

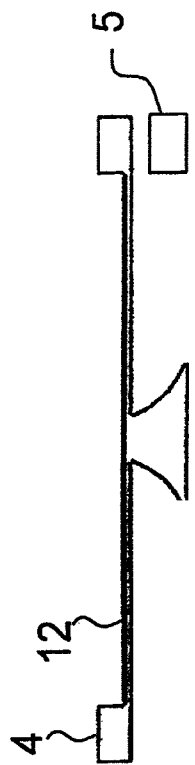
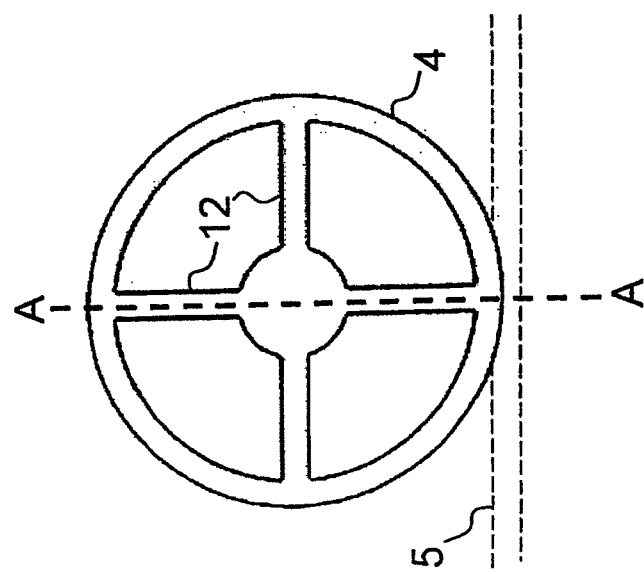
Fig. 16A
Fig. 16B

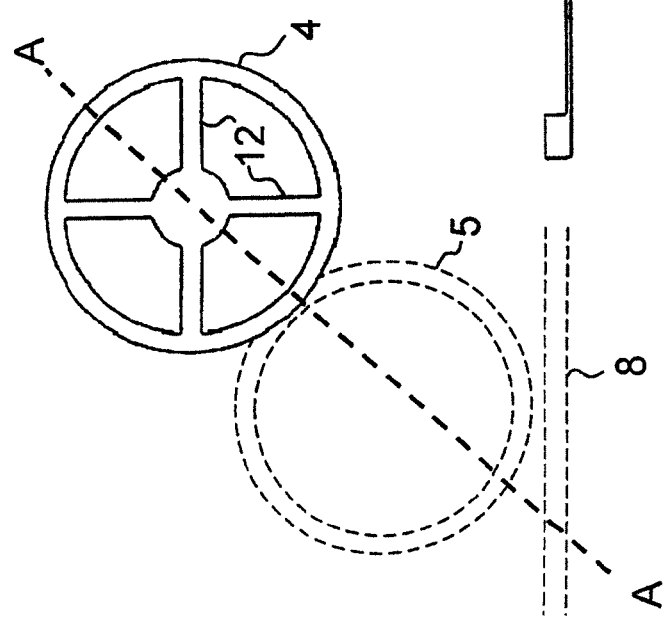
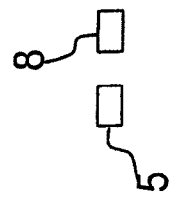
Fig. 17C
Fig. 17B
Fig. 17A

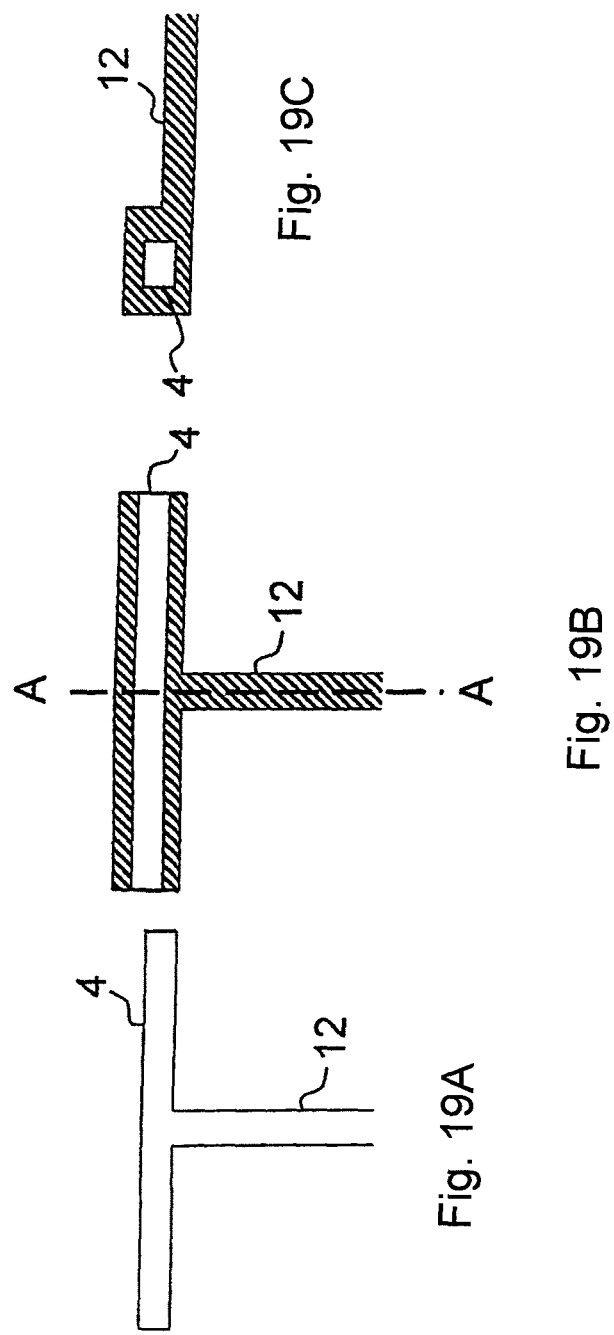

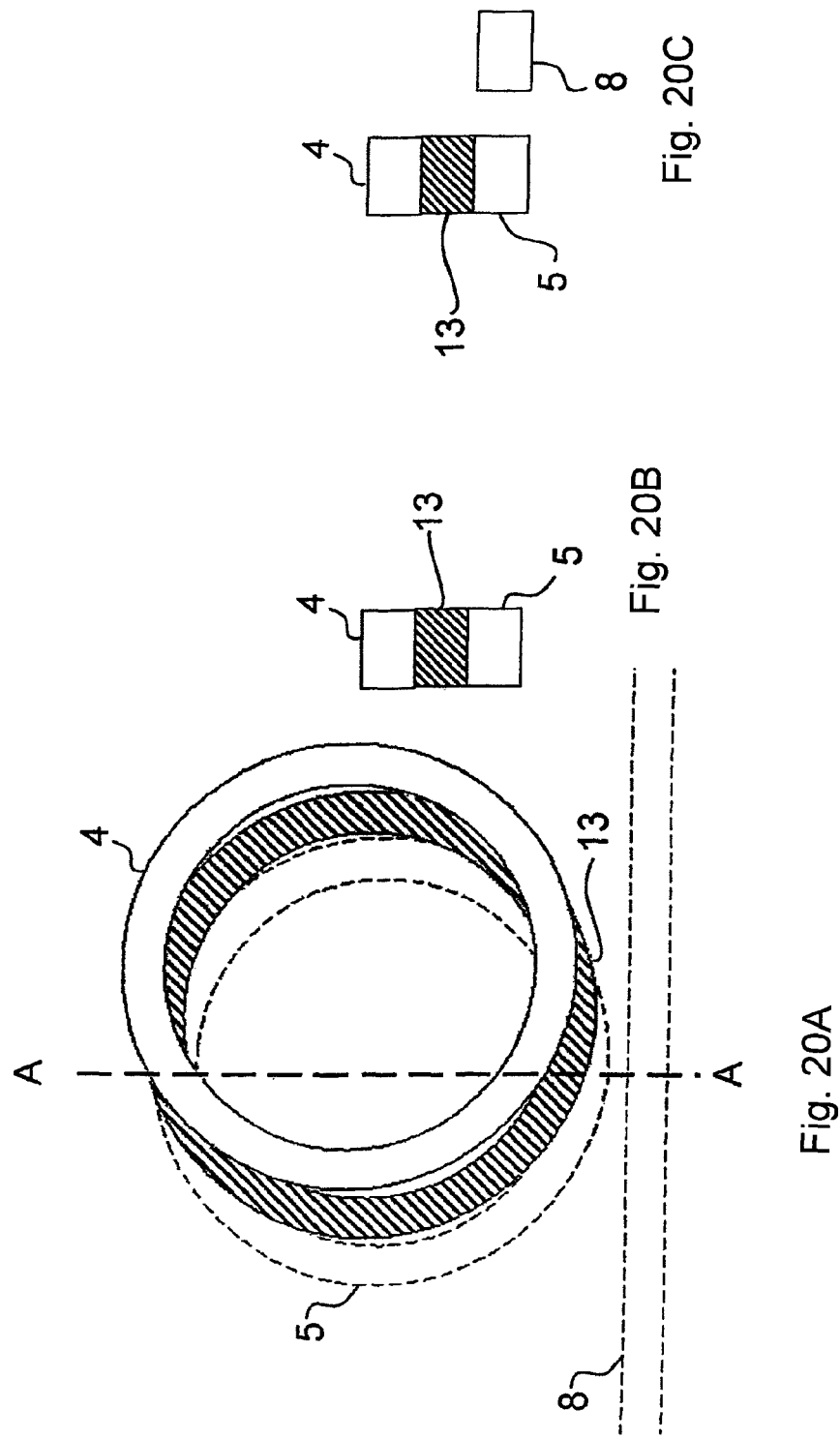

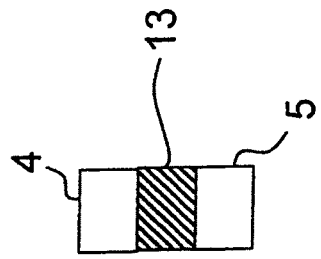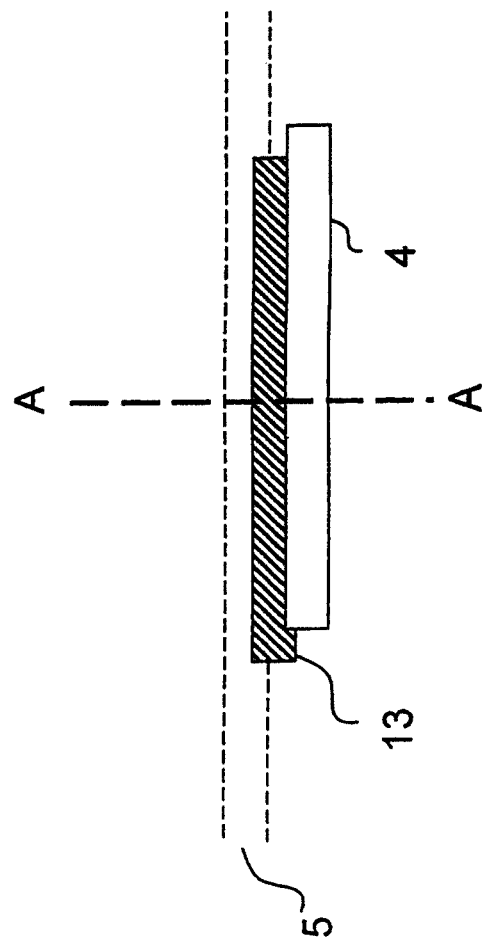

OPTICAL SENSOR

CROSS-REFERENCE TO RELATED APPLICATIONS

The present application is a national phase application of PCT application PCT/EP2009/007302 filed pursuant to 35 U.S.C. §371, which claims priority to DE 10 2008 050 767.9, filed Oct. 9, 2008. Both applications are incorporated herein by reference in their entirety.

TECHNICAL FIELD

The invention relates to an optical sensor for detecting a substance.

BACKGROUND

Sensors for detecting substances are known from the prior art, for example from the field of biosensors, whose function is based on the fact that a substance to be detected is accumulated at a functional surface, that is, is absorbed by this surface, wherein the functional surface forms a selective receptor. Information on the presence, the concentration or the lack of the substance which may be accumulated by the functional surface can then be acquired from the intensity or thickness of an accumulation at the functional surface.

SUMMARY

The present invention is directed to developing a corresponding sensor that permits a purely optical readout to enable a measurement of remote electrical or electronic components.

In some embodiments, an optical sensor for detecting a substance includes a first waveguide as well as a second waveguide that is optically coupled to the first waveguide via a directional coupler. The sensor has a functional surface in a region of the directional coupler for accumulating or storing the substance to be detected so that an intensity of a coupling arranged by the directional coupler between the first waveguide and the second waveguide can be changed by the accumulating or storing of this substance. In some embodiments, at least the first waveguide extends in a freely floating manner over a coupling path covered by the directional coupler, that is, forming a boom or a bridge, or rests there only on a swellable material absorbing the substance at least regionally. A directional coupler is defined in this respect as a region of an assembly of two waveguides in which they are guided so close to one another that a coupling takes place there by an overlap of evanescent fields of the waveguides. The coupling path defined here by the arrangement of the first waveguide in a freely floating manner or resting on the swellable material can in this respect extend over the total directional coupler or also only form a part section of the directional coupler. In the specific case that both named waveguides include rings that are closed in themselves, the coupling path can also extend over the total waveguide.

If this optical sensor, more precisely the functional surface of the sensor, is brought into contact with the substance to be detected, the coupling between the first and second waveguides changes due to the accumulation or storage of the substance on or by the functional surface, which in turn influences an optical signal transported by the waveguides such that it can be determined by a detection of an optical output signal whether and in which quantities the substance to be detected has come into contact with the functional surface. For this purpose, and in some embodiments, the sensor expediently configured as an integrated optical system or including an integrated optical system can include a feed waveguide coupled to a light source, for example to a laser diode, and an output waveguide coupled to a light sensitive element, for example to a photodiode. In this respect, the feed waveguide can be given by the first waveguide or by the second waveguide so that a comparatively simple design results. In other embodiments of the invention, the feed waveguide can also only be optically connected to the first waveguide or to the second waveguide, for example via a further directional coupler. A sensitivity of a readout apparatus of the sensor formed by the waveguides can thereby be increased under certain circumstances. In the same way, the output waveguide can accordingly be given by the second waveguide or by the first waveguide or can alternatively only be optically coupled to the second waveguide or to the first waveguide, for example via a further directional coupler.

Provided that the first waveguide and/or the second waveguide does/do not serve as a feed waveguide or as an output waveguide, but is/are rather only optically coupled thereto, the first waveguide and/or the second waveguide can also be configured as a waveguide ring closed in itself. Such a waveguide ring shows resonant properties which then depend very sensitively on the intensity of the coupling between the first waveguide and the second waveguide. A measured signal decoupled from the output waveguide then shows a particularly clear dependence on the quantity or concentration of the substance which has come into contact with the functional surface.

In some embodiments, at least one of the named waveguides is configured as a single mode waveguide. In some embodiments, this applies to all of the waveguides. Irregularities can thereby be avoided which could otherwise be caused by time of flight differences between different modes due to a dispersion of the waveguides. A waveguide is called single mode when only one mode has room in the waveguide with respect to a transverse field distribution for the polarization used, that is, in particular for at least one of two possible polarizations.

In some embodiments, the first waveguide extends in a freely floating manner within the coupling path, wherein the functional surface that is realized by coating with a selective receptor can be formed by a surface layer of this first waveguide or can form a surface layer of the first waveguide. In this respect, and in some embodiments, this surface layer covers at least a part of the coupling path. A dependence of the coupling between the first waveguide and the second waveguide on the quantity of the substance to be detected absorbed by the functional surface can then already be achieved in that this substance influences an evanescent field of at least the first waveguide.

In accordance with some embodiments, the first waveguide is guided in a vicinity of the coupling path so that a spacing between the first waveguide and the second waveguide can be changed there by a deformation or movement of the first waveguide or of a deflectable carrier of the first waveguide. The coupling between the first waveguide and the second waveguide can therefore be changed in a simple manner by changing the spacing between these waveguides. A simple and reliable measuring principle can therefore be realized in that the sensor is set up so that the accumulation or storing of the substance to be detected at or by the functional surface changes the spacing. This can be realized in various manners as will be shown in the following. In this respect, a change of the spacing between the waveguides is in the present invention in each case designated as a change of a spacing between a waveguide core of the first waveguide and a waveguide core of the second waveguide. In some embodiments, the sensor is designed so that the accumulation or storing of the substance to be detected has the consequence of a static change of the spacing, for example by a static deflection.

The functional surface can thus include for this purpose a surface layer of the deflectable carrier of the first waveguide, provided that the first waveguide is held by such a carrier which can be configured as a boom or as a cantilever. The deformation or movement of the first waveguide, which has the consequence of changing the spacing between the first waveguide and the second waveguide, can then be caused by a mechanical tension in the first waveguide or in the carrier of the first waveguide—typically due to a changed surface tension—which is in turn caused by the substance to be detected which is accumulated or stored on or in the functional surface. In some embodiments, the functional surface is realized by a coating applied only one side of the cantilever and/or of the first waveguide and at least by an asymmetrical coating so that the accumulation or storing of the substance to be detected effects a deformation.

In some embodiments, in which the first waveguide is deformable or movable, the functional surface can be formed by a swellable material that carries the first waveguide or a part of the first waveguide and is at least regionally suitable for receiving the substance to be detected. A movement or deformation of the first waveguide that changes the coupling between the first waveguide and the second waveguide can be caused in that the substance to be detected is stored in the swellable material and thereby a volume change or a swelling of the swellable material is caused. In this respect, e.g. a polymer can be used as the swellable material which can absorb a specific solvent and thereby swell up. If the first waveguide is termed as resting only on the swellable material in connection with the last named embodiment of the invention, this does not naturally preclude the fact that the swellable material in turn lies on a solid base. A further material layer could also be arranged between the swellable material and a core of the first waveguide. What is decisive is the movability of the first waveguide in dependence on an swelling or going down of the named swellable material.

In some embodiments, a simple design of the sensor results when it includes a substrate that carries the first waveguide and the second waveguide. The substrate can e.g. be a semiconductor substrate which can in turn be given by a part of a wafer typically formed of silicon. In some embodiments, the waveguides are separated from the substrate by at least one buffer layer, for example of $SiO_2$. This buffer layer can be recessed in the region of the directional coupler so that at least the first waveguide is cut out there in order to form a surface of attack for the substance to be detected which is as large as possible and freely floating in the region of the coupling path and/or to have the required clearance for movement.

In some embodiments, the first waveguide and the second waveguide can extend in a single plane or alternatively in two planes separated from one another by a buffer layer, with the buffer layer being able to be formed from $SiO_2$, for example. By an arrangement in a single plane, a particularly simple design can be realized, whereas an arrangement in two planes under certain circumstances allows a smaller spacing to be observed between the first waveguide and the second waveguide, which can be of advantage with respect to a coupling which is as intense as possible.

BRIEF DESCRIPTION OF THE FIGURES

FIGS. 12A and 12B show a plan view and a cross-sectional view taken along section line A-A, respectively of a section of an optical sensor in a further embodiment of the invention.

FIGS. 13A and 13B show a plan view and a cross-sectional view taken along section line A-A, respectively of a section of an optical sensor in a further embodiment of the invention.

FIGS. 14A and 14B show a plan view and a cross-sectional view taken along section line A-A, respectively of a section of an optical sensor in a further embodiment of the invention.

FIGS. 15A and 15B show a plan view and a cross-sectional view taken along section line A-A, respectively of a section of an optical sensor in a further embodiment of the invention.

FIGS. 16A and 16B show a plan view and a cross-sectional view taken along section line A-A, respectively of a section of an optical sensor in a further embodiment of the invention.

FIGS. 17A, 17B and 17C show a plan view, a cross-sectional view taken along section line A-A, and another cross-sectional view, respectively, of a section of an optical sensor in a further embodiment of the invention.

FIGS. 19A, 19B and 19C illustrate construction details of the optical sensors of FIGS. 11-17. (FIGS. 20A, 20B and 20C show a plan view, a cross-sectional view taken along section line A-A and another cross-sectional view, respectively, of an optical sensor in another embodiment of the invention.

FIGS. 21A and 21B show a plan view and a cross-sectional view taken along section line A-A, respectively of an optical sensor in another embodiment of the invention.

DETAILED DESCRIPTION

Figure 1:
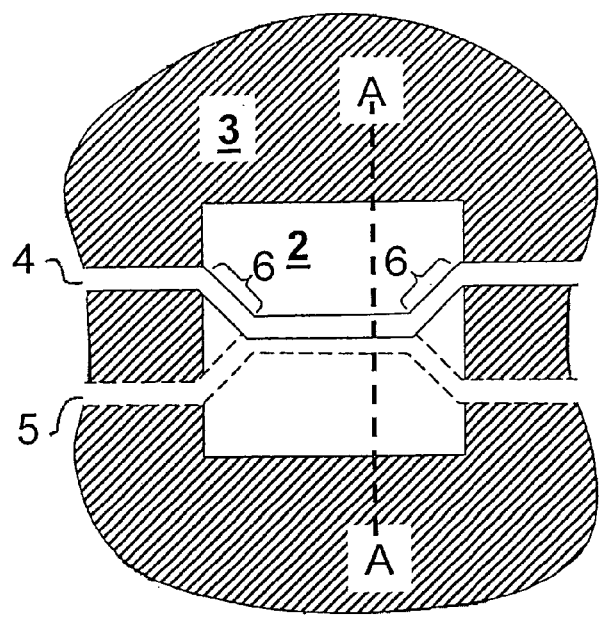
FIG. 1 is a plan view of section of an optical sensor in an embodiment of the invention.
Figure 2:
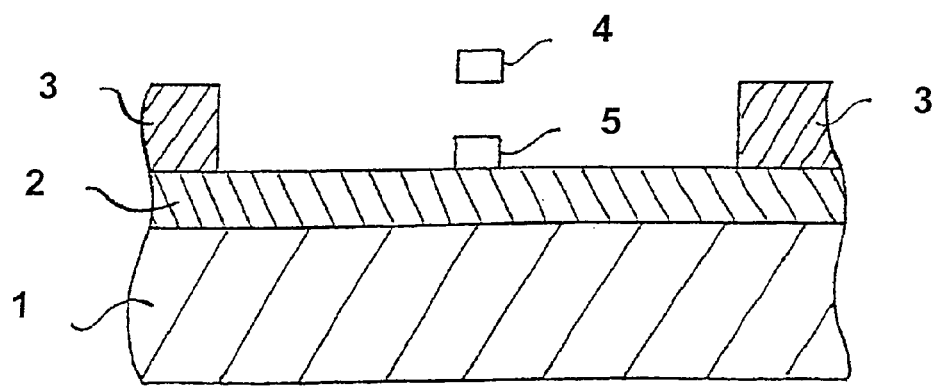
FIG. 2 is a cross-section through the optical sensor of FIG. 1 at a point designated by A-A there.

The optical sensor, of which a respective section is shown in FIGS. 1 and 2, like all other optical sensors described here, forms an integrated optical system which can be complemented by further components such as a light source, a light sensitive element and evaluation electronics. The optical sensor includes a substrate 1 which is a part of a silicon wafer. A buffer layer of $SiO_2$ is arranged above the substrate 1 and carries a further buffer layer 3 of the same material in the embodiment of FIGS. 1 and 2.

In some embodiments, the optical sensor has a first optical waveguide 4 and a second optical waveguide 5. The first waveguide 4 is carried by the further buffer layer 3 and the second waveguide 5 rests on the buffer layer 2 lying thereunder. At a point at which the further buffer layer 3 is cut out and forms a window so that the first waveguide 4 extends in a freely floating manner there and forms a bridge, the waveguides 4 and 5 are guided parallel to one another at a small spacing, over one another in the present embodiment. An optical coupling of the waveguides 4 and 5 thereby results, said waveguides thus forming a directional coupler within the window in the buffer layer 3.

The first waveguide 4 has, at least in sections 6, a functional surface in which the first waveguide 4 carries a coating of a selective receptor at an upper side or lower side of the waveguide 4. In some embodiments, the functional surface preferably or exclusively adsorbs a specific substance to be detected. If the optical sensor—more precisely the functional surface in the sections 6—comes into contact with this substance, the substance to be detected accumulates there, which has the consequence of mechanical tension and thus a deformation of the first waveguide 4. In this respect, the first waveguide 4 is guided in the region of the directional coupler which forms a coupling path such that a spacing between the waveguides 4 and 5 changes by such a deformation there. An intensity of the optical coupling between the first waveguide 4 and the second waveguide 5 thus in turn changes.

The optical sensor described up to this point can therefore be utilized for detecting the named substance in that the first waveguide 4 is used as a feed waveguide and is connected to a light source, for example to a laser diode, whereas the second waveguide 5 is used as an output waveguide and is coupled at one end to a light sensitive element, for example to a photodiode. A signal detected by the light sensitive element will then depend very sensitively on the intensity of the coupling between the two waveguides 4 and 5 and thus on a presence or lack or more precisely on a concentration of the substance to be detected in a direct vicinity of the functional surface on the first waveguide 4. The waveguides 4 and 5 can naturally also be swapped with respect to their use as a feed waveguide and as an output waveguide.

Figure 3:
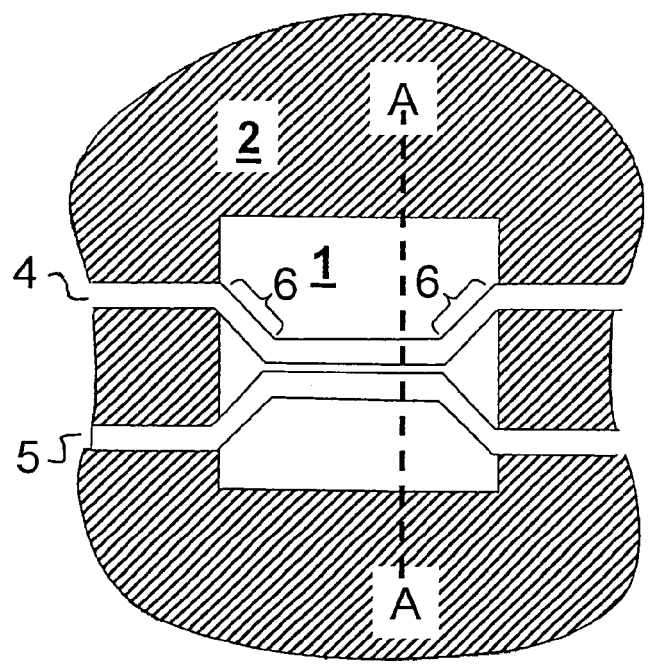
FIG. 3 is a representation of an optical sensor corresponding to FIG. 1 in another embodiment of the invention.
Figure 4:
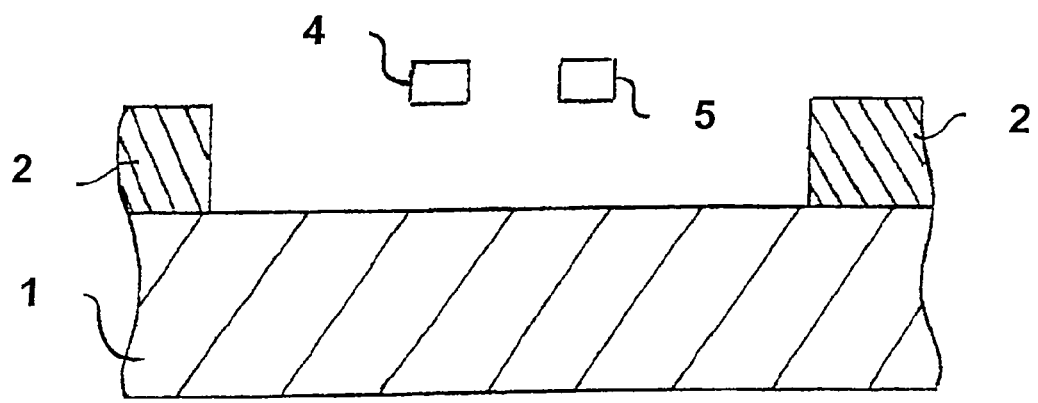
FIG. 4 is a cross-section through the optical sensor of FIG. 3 at a point designated by A-A.

A similar embodiment of an optical sensor is shown in FIGS. 3 and 4, wherein recurring features are here and in the following again provided with the same reference numerals and are no longer described in detail for each embodiment. The optical sensor of FIGS. 3 and 4 differs from the previously described embodiment in that the two waveguides 4 and 5 do not extend in two different planes separated from one another by the further buffer layer 3, but rather in a single plane which is separated from the substrate 1 by a single buffer layer 2. The first waveguide 4 and the second waveguide 5 also form a directional coupler here, with the two waveguides 4 and 5 not being guided over one another there, but rather next to one another. The optical sensor of FIGS. 3 and 4 otherwise corresponds in its function to the previously described sensor. In some embodiments, at least the first waveguide 4 carries a coating at least at points which forms a functional surface in the previously explained sense within the window which is here cut out in the buffer layer 2 and defines the region of the directional coupler.

The waveguides 4 and 5 of the described embodiments are, as also in all waveguides from the optical sensors described in the following, single mode waveguides whose cross-section is dimensioned so that only one mode can propagate for each polarization direction there.

A modification of the embodiments from FIGS. 1 to 4 provides that the first waveguide 4 does not extend in a freely floating manner in the region of the directional coupler, that is, within the window in the respective buffer layer 3 or 2, but rather instead rests on a swellable material there which then fills a space between the waveguides 4 and 5 when the first waveguide 4 is guided over the second waveguide 5 or between the first waveguide 4 and the substrate 1. In this case, the swellable materials, instead of a coating of the first waveguide 4, forms a functional surface for storing the substance to be detected in the swellable material. The swellable material can be a polymer, for example. A contact of the functional surface of the swellable material with the substance to be detected then results in a volume change of the swellable material which swells and thereby raises the first waveguide 4 and increases its spacing from the second waveguide 5. In this case, the contact with the substance to be detected also has the consequence that the intensity of the coupling between the two waveguides 4 and 5 changes, which can be utilized for detecting the substance in a previously described manner.

Figure 5:
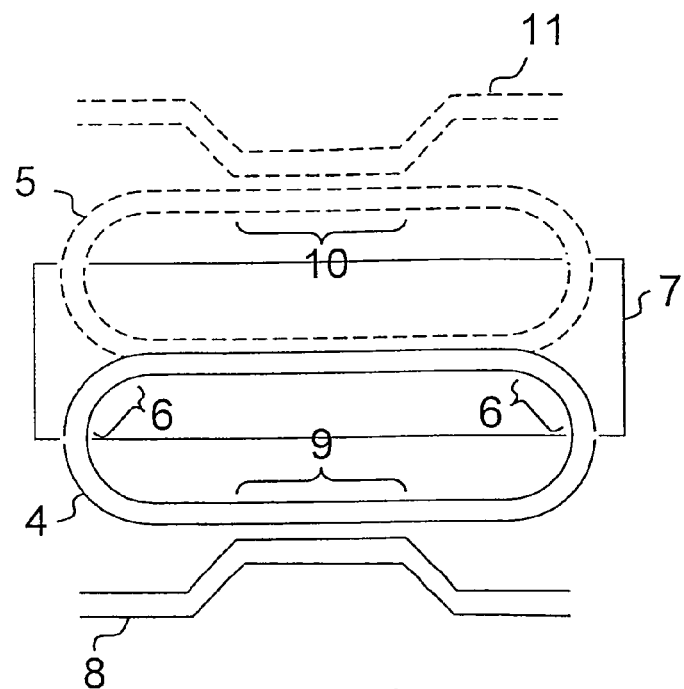
FIGS. 5 to 11 are plan views of a section of an optical sensor in different further embodiments, wherein in each case there only waveguides covered by the sensor shown as well as an outline of a window are shown within which a buffer layer is cut out.

The sensor shown in FIG. 5 corresponds in its structure largely to the sensor of FIGS. 1 and 2, except that the first waveguide 4 and the second waveguide 5 are each configured as a waveguide ring closed in itself. In addition, a feed waveguide 8 is provided which extends with the first waveguide 4 in a plane, which is coupled at one end to a light source, not shown, and which is coupled via a further directional coupler 9 to the first waveguide 4 to feed light into it. In a corresponding manner, the second waveguide 5 is coupled via an additional directional coupler 10 to an output waveguide 11 which is configured as an independent waveguide and to which in this case the light sensitive element, likewise not shown, is connected.

In some embodiments, the first waveguide 4 and the second waveguide 5 each form a microring resonator, wherein the coupling between these microring resonators results in a splitting of optical resonances of symmetrical or antisymmetrical total mode distributions. The change of the coupling by a deformation of at least the first waveguide 4 in a previously described manner results here in a change of a splitting frequency which can be measured via a measured signal decoupled from the output waveguide 11.

Instead of the output waveguide 11, which could also be omitted, the feed waveguide 8 itself can also be used for decoupling the measured signal. In another respect, it also applies in an analog manner to the previously described embodiments that the light sensitive element for detecting the measured signal could be arranged at an output of the first waveguide 4 instead of an end of the second waveguide 5.

Figure 6:
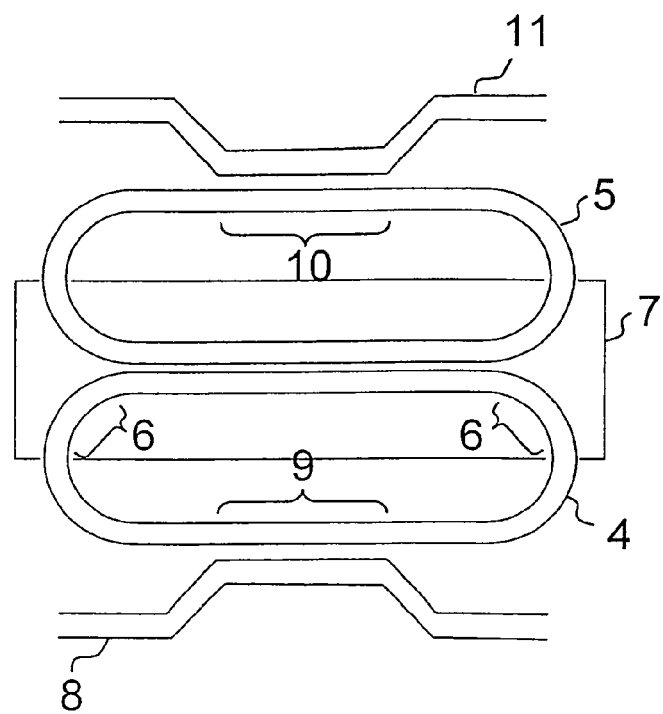

The embodiment shown in FIG. 6 differs from the sensor of FIG. 5 only by the arrangement of all waveguides, that is of the first waveguide 4, of the second waveguide 5, of the feed waveguide 8 and of the output waveguide 11, in a single plane so that this sensor has a cross-section corresponding to FIG. 4 in a region of the directional coupler between the waveguides 4 and 5 instead of a cross-section of the kind shown in FIG. 2. The first waveguide 4 is here also provided at least in sections 6 with a coating which there forms a functional surface. In this respect, the waveguides 4 and 5 can naturally be swapped with respect to their functions or both can be provided with a corresponding coating.

Figure 7:
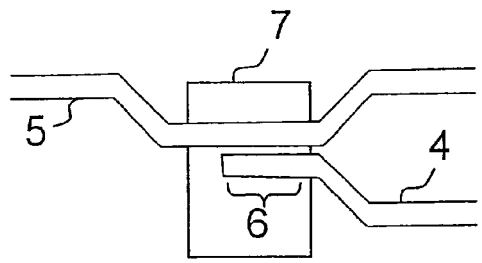

A plan view of an optical sensor in a further embodiment of the invention is shown in FIG. 7. This sensor likewise has a cross-section corresponding to FIG. 4. In this respect, the first waveguide 4, which here acts as an output waveguide, differing from the second waveguide 5, which is here connected to the light source, not shown, does not form a bridge, but only a boom or cantilever suspended at one end, and indeed in the section 6 in which the first waveguide 4 has the functional surface which results in a bending of the boom in the event of an accumulation of the substance to be detected.

Figure 8:
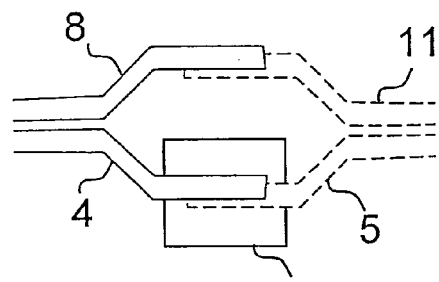
Figure 9:
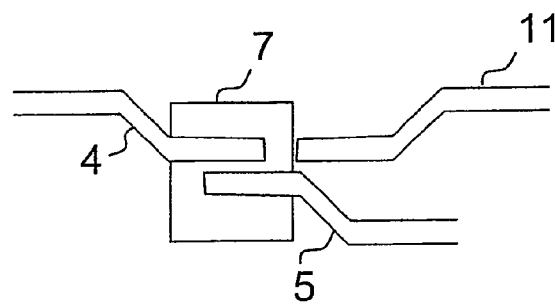
Figure 10:
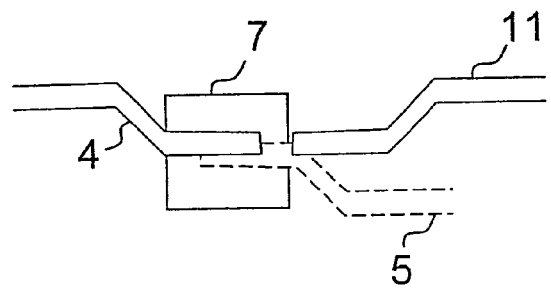

Further embodiments are shown in a corresponding representation in FIGS. 8 to 10, wherein lower lying waveguides are shown with dashed borders. The sensors of FIGS. 8 and 10 in this respect show a cross-section which corresponds to FIG. 2, whereas the sensor of FIG. 9 has a cross-section of the kind shown in FIG. 4. The sensor of FIG. 8 has, in addition to an optical path formed by the first waveguide 4 and the second waveguide 5, a further optical path which is correspondingly guided, but which has an unchanging coupling between a feed waveguide 8 and an output waveguide 11. The sensors of FIGS. 9 and 10 each show an additional output waveguide 11 which is connected via a butt coupling to the first waveguide 4 and thus allows an additional detection of a deflection or deformation of the first waveguide 4.

Figure 11:
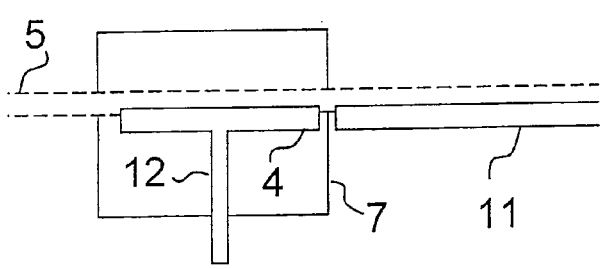

A further embodiment having a first waveguide 4 lying in a higher plane and a second waveguide 5 lying thereunder is shown in FIG. 11. The first waveguide 4, which lies completely within the window having the outline 7, also extends in a freely floating manner in this embodiment, for which purpose it is held by a deflectable carrier 12 in this case. Instead of the first waveguide 4, the carrier 12 is provided here with the coating forming the functional surface, typically at an upper side. A contact with the substance to be detected here results in a bending of the carrier 12, which in turn has the consequence of a change of the spacing between the first waveguide 4 and the second waveguide 5. A measured signal can here be taken from a second end of the second waveguide 5 or alternatively or additionally from an end of an additional output waveguide 11 which can be connected via a butt coupling to the first waveguide 4. This butt coupling will also change with a deflection of the carrier 12, which results in a further influencing of an output signal through the substance accumulating at the functional surface.

FIGS. 12A-B, 13A-B, 14A-B, 15A-B, 16A-B and 17A-C show plan and cross-sectional views of different embodiments of optical sensors. Each of these sensors have a first waveguide 4 that is coupled via a directional coupler to a second waveguide 5, wherein the intensity of a coupling between the first waveguide 4 and the second waveguide 5 depends on the quantity of a substance to be detected accumulated at a functional surface. In this respect, the first waveguide 4 in each of these embodiments is a waveguide ring that is closed in itself, which is held with four arms by a carrier 12 arranged within the waveguide ring and which otherwise extends in a freely floating manner. The four arms of the carrier 12 are provided at an upper side with a coating of the described kind and thereby form a functional surface for accumulating the substance to be detected. In these embodiments, an adsorption of this substance by the functional surface results in a raising or a lowering of the first waveguide 4 so that the intensity of the coupling between the first waveguide 4 and the second waveguide 5 changes.

In the embodiments of FIGS. 12A-B and 16A-B, the second waveguide 5 serves both as a feed waveguide in which light of a light source, not shown, is fed and as an output waveguide for which purpose it is connected at another end to a light-sensitive element, likewise not shown. A signal to be detected there depends on the intensity of the coupling to the first waveguide 4 and thus allows conclusions on the quantity of the substance adsorbed at the functional surface.

In the embodiment of FIGS. 14A and 14B an additional ring waveguide is provided that is held in a similar manner to the first waveguide 4. This ring waveguide serves as a second waveguide 5 and is accordingly coupled to the first waveguide 4 via a directional coupler. In addition, the waveguide 4 is coupled via a further directional coupler to a feed waveguide 8 into which light of a light source, not shown, is fed and which simultaneously serves as an output waveguide for decoupling a measured signal. The dependence of the measured signal decoupled from the second feed waveguide 8 on the position of the first waveguide 4 is amplified here by the design of the second waveguide 5 which is likewise provided with a functional surface and is movable as a ring waveguide.

In the embodiments of FIGS. 13A-B, 15A-B and 17A-C, the second waveguide 5 that is coupled via a directional coupler to the first waveguide 4 is configured as a waveguide ring which is in turn coupled via a further directional coupler to an additionally provided feed waveguide 8. In this embodiment, the feed waveguide 8 serves both the feeding of light from a light source, not shown, and the decoupling of a measured signal which is measured by a light-sensitive element, not shown. These arrangements also result in a highly sensitive dependence of the measured signal decoupled from the feed waveguide 8 on the position of the first waveguide 4 which changes with an accumulation of the substance to be detected at the functional surface.

Figure 18:
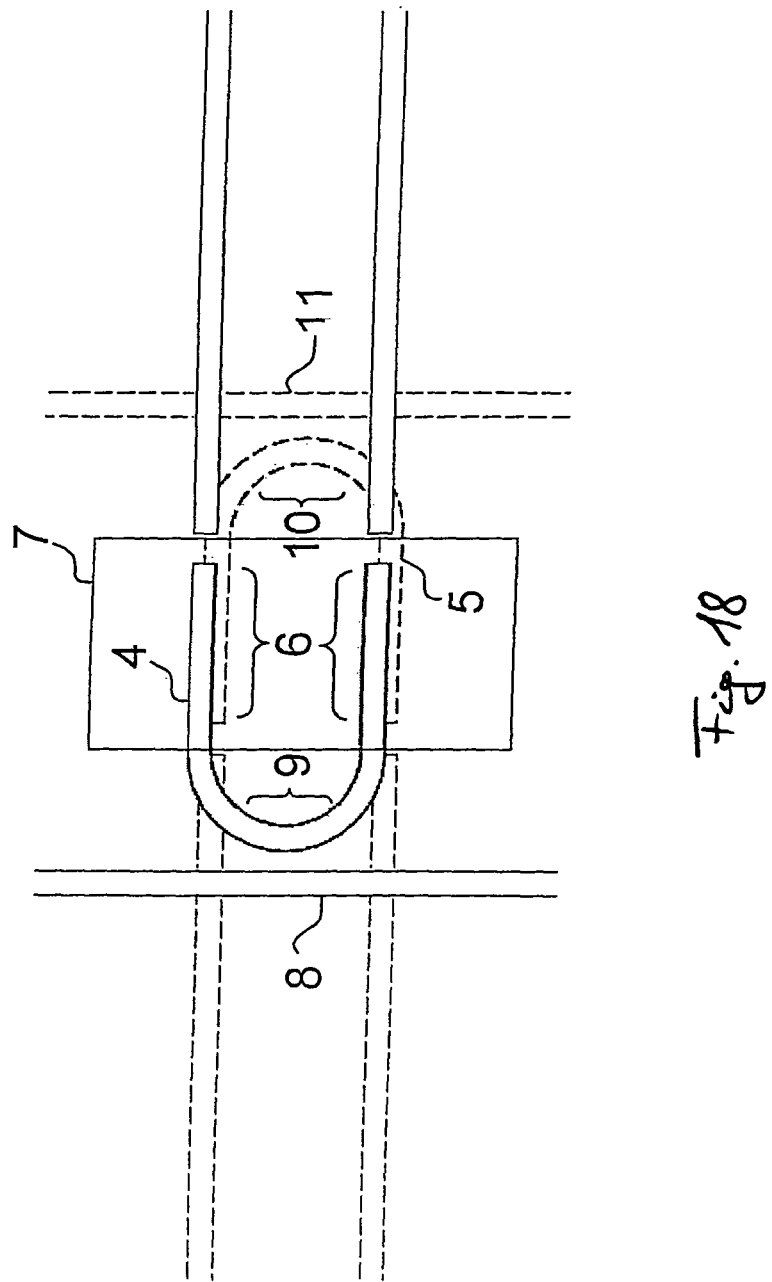
FIG. 18 is a further embodiment for an optical sensor in a representation corresponding to FIGS. 5 to 11.

In FIG. 18, a further example for a similar optical sensor is shown in a representation corresponding to FIGS. 5 to 11 in which recurring features are again provided with the same reference numerals. Here, the first waveguide 4 is coupled at two points via a respective directional coupler to the second waveguide 5, wherein the first waveguide 4 forms two booms in sections 6 defined by the directional couplers within a window of a buffer layer and there has a functional surface in the previously described sense at an upper side or at a lower side. The first waveguide 4 is coupled via a further directional coupler 9 to a feed waveguide 8, whereas the second waveguide 5 disposed thereunder is coupled via an additional directional coupler 10 to an output waveguide 11. In addition, in this embodiment, further waveguides are provided which are coupled via butt couplings to the first waveguide 4 or to the second waveguide 5 and thereby allow a readout of further information.

In FIGS. 19A-C, a section of a sensor of the kind shown in FIG. 11 is shown in two different embodiments. In each case, the first waveguide 4 is shown which is held by a carrier 12 in the form of a deflectable arm, wherein the functional surface of the respective sensor is given by a coating of this carrier 12. In the variant shown in FIGS. 19A-C, the carrier 12 is made from the same material as the first waveguide 4, for example from silicon. In the variant shown in FIG. 19C, the first waveguide 4 includes a waveguide core which can likewise be formed from silicon, wherein this waveguide core is here embedded in a different material, for example a polymer, from which the carrier 12 is also formed.

In FIGS. 20A-C, a further embodiment of an optical sensor is shown in which both the first waveguide 4 and the second waveguide 5 are formed by a respective waveguide ring. The second waveguide 5, which is designed as stationary, is coupled via a directional coupler to a feed waveguide 8 so that this sensor shows a topology very similar to the embodiment of FIGS. 15A-B. In contrast to FIGS. 15A-B, the first waveguide 4 is not configured as freely floating, but instead rests only on a swellable material 13 that separates it from the second waveguide 5. The spacing between the first waveguide 4 and the second waveguide 5 also changes here in dependence on whether and in what concentration the sensor comes into contact with the substance to be detected. For this purpose, the swellable material 13 here forms the functional surface through which in this embodiment the substance to be detected is stored in the swellable material 13, which effects a volume change of the swellable material 13. The change in spacing resulting from this between the waveguides 4 and 5 is in turn accompanied by a change of the optical coupling between these waveguides 4 and 5, which influences a measured signal decoupled from the feed waveguide 8 in the manner already described and thus allows a detection of the named substance.

FIGS. 21A-B shows a waveguide arrangement in a last embodiment which shows a layer structure corresponding to the embodiment of FIGS. 20A-C having a swellable material 13 arranged between the first waveguide 4 and the second waveguide 5. Here, both the first waveguide 4 and the second waveguide 5 have a straight course, wherein the second waveguide 5 simultaneously serves as a feed waveguide and as an output waveguide and for this purpose is coupled at a respective one end to a light source, not shown, and to a light-sensitive element, likewise not shown. In the embodiments of FIGS. 20A-C and 21A-B, a respective polymer can be used as the swellable material 13 which is able to absorb e.g. a specific solvent type and so permits its detection.

In some embodiments, the determination described here of a change of the evanescent couplings between waveguides, of which one at least one is movable, allows a very exact readout of a deflection state of the movable waveguide since the coupling intensity in an evanescent coupling between waveguides depends exponentially on the spacing between the waveguides. The deflection state can in this respect be defined by a bending of the cantilevers carrying the waveguides or of the waveguides themselves, wherein this bending can e.g. be caused by surface tensions which are in turn influenced by specific bonding events. In contrast to the couplings via directional couplers, higher losses are to be expected with butt couplings due to a propagation of the respective signal as a free beam over a certain distance. In contrast to the measurement of the butt coupling, on a use of evanescent coupling, a direct increase in the sensitivity is also possible by extending the coupling distance. A coupler of the kind proposed here also shows a high sensitivity with respect to a change of waveguide dimensions by specific accumulation of foreign bodies at the waveguides. This sensitivity can be further increased by an embedding of the coupler structure in optical resonators, for example by structures of the kind shown in FIGS. 5 and 6.

In some embodiments, a plurality of sensors can be read out after one another by a separation possible with sensors of the proposed kind of a complex analysis unit from a purely optical sensor unit simple with respect thereto so that inexpensive solutions can be achieved. A use in protected zones which have to remain free of electric or electronic components also becomes possible by the purely optical control of the sensor units.

The invention claimed is:

1. An optical sensor for detecting a substance, the optical sensor comprising:
   a first waveguide;
   a second waveguide optically coupled to the first waveguide within a coupling path, thereby forming a directional coupler between the first waveguide and the second waveguide; and
   a functional surface near the directional coupler that is configured to accumulate or store a substance to be detected such that an intensity of a coupling between the first waveguide and the second waveguide can be changed by the substance accumulated or stored on the functional surface;
   wherein the first waveguide is guided in a vicinity of the coupling path such that a spacing between the first waveguide and the second waveguide is changeable there by a deformation or movement of the first waveguide or of a carrier of the first waveguide, and
   wherein at least the first waveguide extends in a freely floating manner over the coupling path covered by the directional coupler or rests there only on a swellable material absorbing the substance.

2. The optical sensor of claim 1, wherein the spacing between the first waveguide and the second waveguide is changeable by accumulating or storing the substance to be detected at or by the functional surface.

3. The optical sensor of claim 1, wherein the first waveguide extends in a freely floating manner within the coupling path and the functional surface is formed on at least one of a surface layer of the first waveguide or a deflectable carrier that which holds the first waveguide.

4. The optical sensor of claim 1, wherein the functional surface is formed by the swellable material.

5. The optical sensor of claim 1, further comprising a substrate that carries the first waveguide and the second waveguide.

6. The optical sensor of claim 5, wherein the first waveguide and the second waveguide are separated from the substrate via a buffer layer.

7. The optical sensor of claim 6, wherein the buffer layer is cut out in a region of the directional coupler so that at least the first waveguide is undercut there.

8. The optical sensor of claim 1, wherein the first waveguide and the second waveguide extend in a single plane.

9. The optical sensor of claim 6, wherein the first waveguide and the second waveguide extend in two planes separated from one another by the buffer layer.

10. The optical sensor of claim 1, further comprising a feed waveguide coupled to a light source and an output waveguide coupled to a light-sensitive element.

11. The optical sensor of claim 10, wherein the feed waveguide is formed by the first waveguide or by the second waveguide or is optically coupled to the first waveguide or to the second waveguide.

12. The optical sensor of claim 10, wherein the output waveguide is formed by the second waveguide or by the first waveguide or is optically coupled to the second waveguide or to the first waveguide.

13. The optical sensor of claim 1, wherein the first waveguide is configured as a waveguide ring closed in itself.

14. The optical sensor of claim 1, wherein the second waveguide is configured as a waveguide ring closed in itself.

15. The optical sensor of claim 1, wherein the first waveguide is configured as a single-mode waveguide.

16. The optical sensor of claim 1, wherein the second waveguide is configured as a single-mode waveguide.

* * * * *